(12) United States Patent
Bamberg

(10) Patent No.: US 11,207,215 B2
(45) Date of Patent: Dec. 28, 2021

(54) EYE COVERING PILLOW WITH HEAD ATTACHMENT

(71) Applicant: Melissa Bamberg, Loomis, CA (US)

(72) Inventor: Melissa Bamberg, Loomis, CA (US)

( * ) Notice: Subject to any disclaimer, the term of this patent is extended or adjusted under 35 U.S.C. 154(b) by 791 days.

(21) Appl. No.: 15/710,468

(22) Filed: Sep. 20, 2017

(65) Prior Publication Data

US 2018/0008468 A1 Jan. 11, 2018

Related U.S. Application Data

(63) Continuation-in-part of application No. 14/856,404, filed on Sep. 16, 2015, now Pat. No. 10,335,318, which is a continuation-in-part of application No. 12/799,413, filed on Apr. 22, 2010, now Pat. No. 9,138,086.

(60) Provisional application No. 62/396,976, filed on Sep. 20, 2016.

(51) Int. Cl.
*A61F 9/04* (2006.01)

(52) U.S. Cl.
CPC ...................................... *A61F 9/04* (2013.01)

(58) Field of Classification Search
CPC .................................. A61F 9/04; A61F 9/026
See application file for complete search history.

(56) References Cited

U.S. PATENT DOCUMENTS

| 945,839 | A | | 1/1910 | Brisbane | |
|---|---|---|---|---|---|
| 1,380,480 | A | | 6/1921 | Jennings | |
| 2,412,769 | A | | 12/1946 | Easterbrooks | |
| 2,413,828 | A | | 1/1947 | Hirsh | |
| 2,537,768 | A | * | 1/1951 | Laporte | A61F 11/12 2/15 |
| 3,538,508 | A | | 11/1970 | Young | |
| 3,840,918 | A | | 10/1974 | Shave | |
| 3,868,984 | A | * | 3/1975 | Jorgensen | A61F 7/02 607/109 |
| 4,411,263 | A | * | 10/1983 | Cook | A61F 9/04 128/858 |
| 4,420,847 | A | | 12/1983 | Smith | |
| D285,624 | S | * | 9/1986 | Rosenbaum | D16/301 |
| 4,649,908 | A | * | 3/1987 | Ghaly | A61F 9/04 128/858 |

(Continued)

FOREIGN PATENT DOCUMENTS

DE 3920954 A1 * 1/1990 ............... A61F 9/04

*Primary Examiner* — David R Hare
*Assistant Examiner* — Alexis Felix Lopez
(74) *Attorney, Agent, or Firm* — Heisler & Associates

(57) ABSTRACT

The eye covering includes an elongated sleeve filled with media, such as beads. The sleeve is divided into separate cells. Preferably two central cells are provided for covering the eyes with two lateral cells provided for covering ears. End structures on the sleeve are configured with a retainer to allow the end structures to be attached together. One form of retainer is a slit in one of the end structures. The other end structure is fed through this slit so that the sleeve is formed into a circuit which can fit around the head. Another optional retainer includes a loop, such as a tag, joined to one of the end structures with a gap beneath the tag. In one embodiment both a tag and slit are provided so that the opposite end structure can be fed through both the slit and under the tag to hold the ends together.

8 Claims, 2 Drawing Sheets

(56) References Cited

U.S. PATENT DOCUMENTS

| | | | |
|---|---|---|---|
| 4,679,263 A * | 7/1987 | Honer | A47C 7/383 |
| | | | 297/393 |
| 4,779,291 A | 10/1988 | Russell | |
| 4,790,031 A * | 12/1988 | Duerer | A61F 9/02 |
| | | | 128/858 |
| 4,951,337 A | 8/1990 | Hull | |
| 5,127,117 A | 7/1992 | Bridges | |
| 5,572,753 A | 11/1996 | Ruscitto | |
| 5,881,390 A * | 3/1999 | Young | A41D 20/00 |
| | | | 2/209.13 |
| 5,890,487 A * | 4/1999 | Kimmel | A61F 7/02 |
| | | | 128/845 |
| 6,017,606 A * | 1/2000 | Sage | A61F 7/02 |
| | | | 428/102 |
| 6,088,836 A * | 7/2000 | de Cordova | A47C 7/383 |
| | | | 2/15 |
| 6,193,740 B1 | 2/2001 | Rodriguez | |
| 6,363,554 B1 | 4/2002 | Brown | |
| 6,537,308 B2 * | 3/2003 | Burkhart | A61F 7/02 |
| | | | 2/171.2 |
| 6,651,256 B1 | 11/2003 | Swift | |
| 6,656,210 B1 * | 12/2003 | Plewes | A61F 7/02 |
| | | | 128/DIG. 15 |
| D489,749 S * | 5/2004 | Landvik | D16/301 |
| 7,428,763 B2 | 9/2008 | Hightower | |
| D583,605 S | 12/2008 | Krinsky | |
| 7,601,168 B2 | 10/2009 | Koby | |
| 7,657,954 B1 | 2/2010 | Bunkers | |
| 7,767,874 B2 * | 8/2010 | Kellogg | A61F 13/00038 |
| | | | 602/48 |
| 8,239,987 B2 | 8/2012 | Sharp | |
| 8,887,333 B2 | 11/2014 | Cohen | |
| 10,188,214 B2 * | 1/2019 | James | A47C 7/383 |
| 10,426,666 B1 * | 10/2019 | Seidenfeld | A61F 9/04 |
| 2003/0187375 A1 * | 10/2003 | Gaylord | A61F 5/32 |
| | | | 602/26 |
| 2006/0058840 A1 * | 3/2006 | Payne | A61F 13/124 |
| | | | 606/201 |
| 2006/0218688 A1 * | 10/2006 | Cheng | A61F 9/04 |
| | | | 2/12 |
| 2008/0034503 A1 | 2/2008 | Hightower | |
| 2008/0216244 A1 * | 9/2008 | Minton | A47G 9/10 |
| | | | 5/640 |
| 2010/0229275 A1 * | 9/2010 | Wilson | A61F 9/04 |
| | | | 2/15 |
| 2010/0301655 A1 | 12/2010 | Mezger | |
| 2012/0144590 A1 | 6/2012 | Sharp | |
| 2012/0186016 A1 | 7/2012 | Martin | |
| 2012/0210516 A1 * | 8/2012 | Popovic | A47G 9/1081 |
| | | | 5/640 |
| 2013/0227784 A1 | 9/2013 | Holliday | |
| 2013/0312180 A1 | 11/2013 | Moran | |
| 2013/0312192 A1 | 11/2013 | Lee | |
| 2014/0000036 A1 | 1/2014 | Cohen | |
| 2014/0199507 A1 | 7/2014 | Moran | |
| 2016/0120253 A1 | 5/2016 | Schenk | |
| 2017/0264994 A1 * | 9/2017 | Gordon | H04R 1/026 |
| 2018/0055691 A1 * | 3/2018 | Renaud | A61F 7/007 |

* cited by examiner

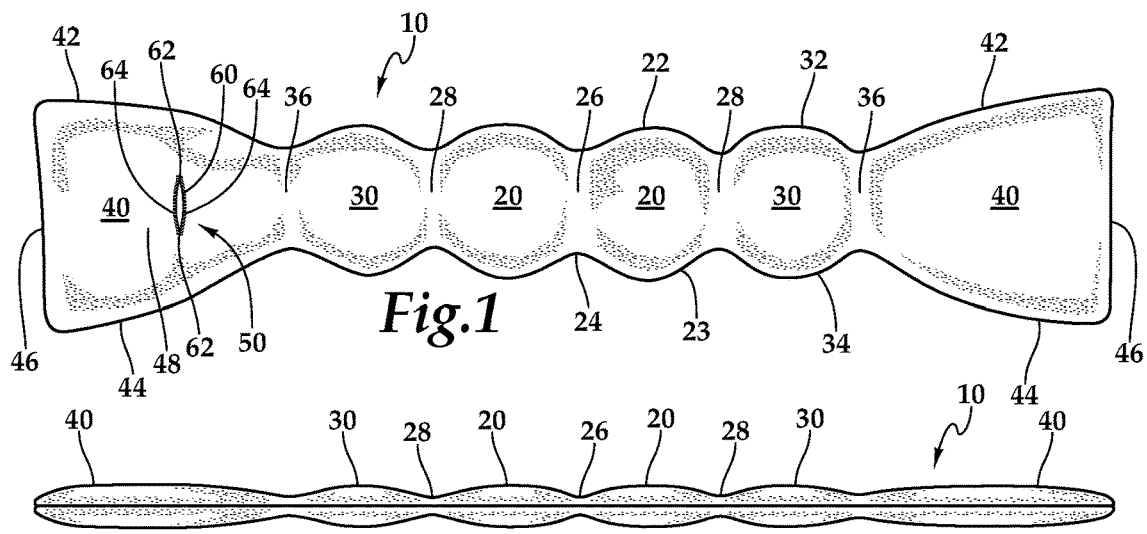
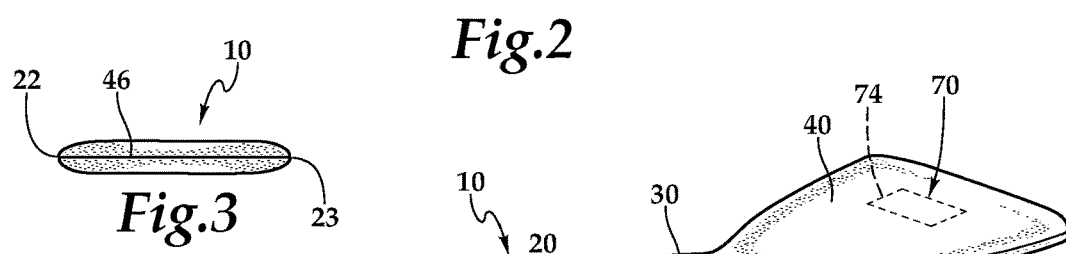
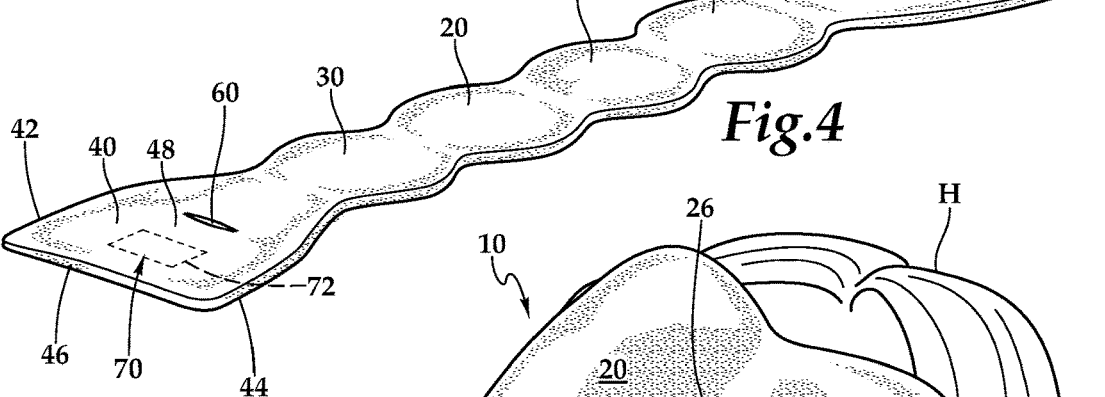
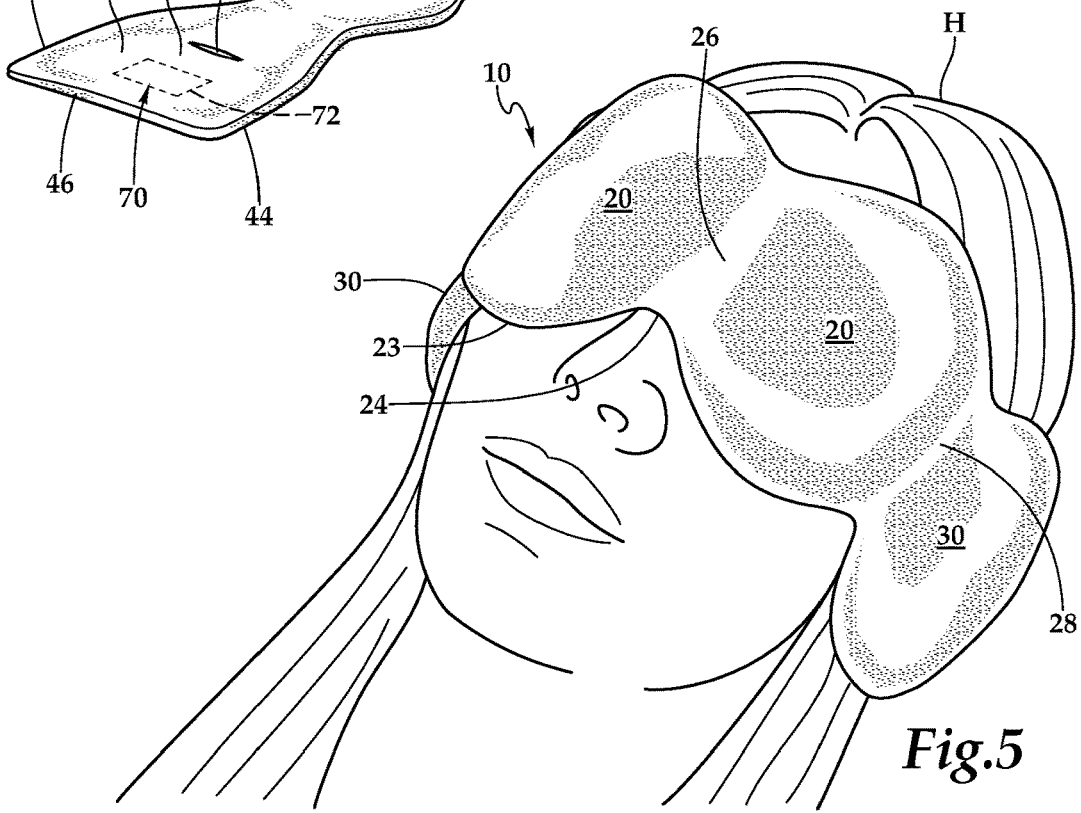

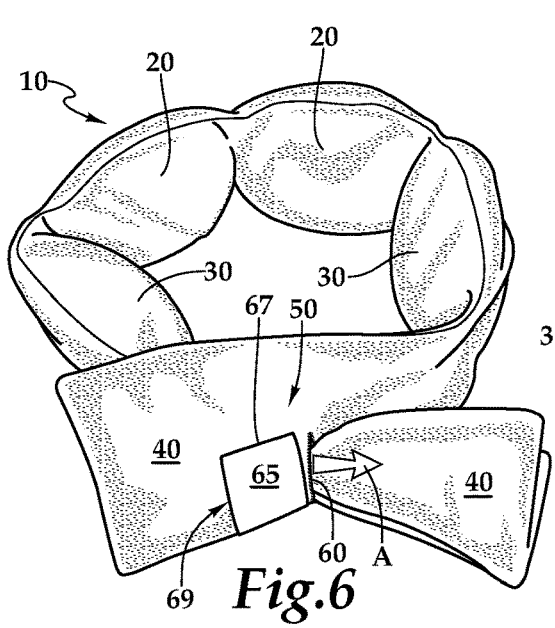
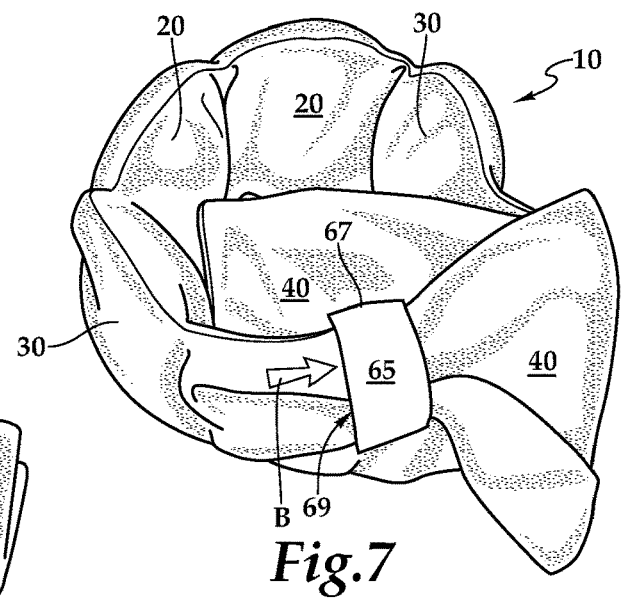
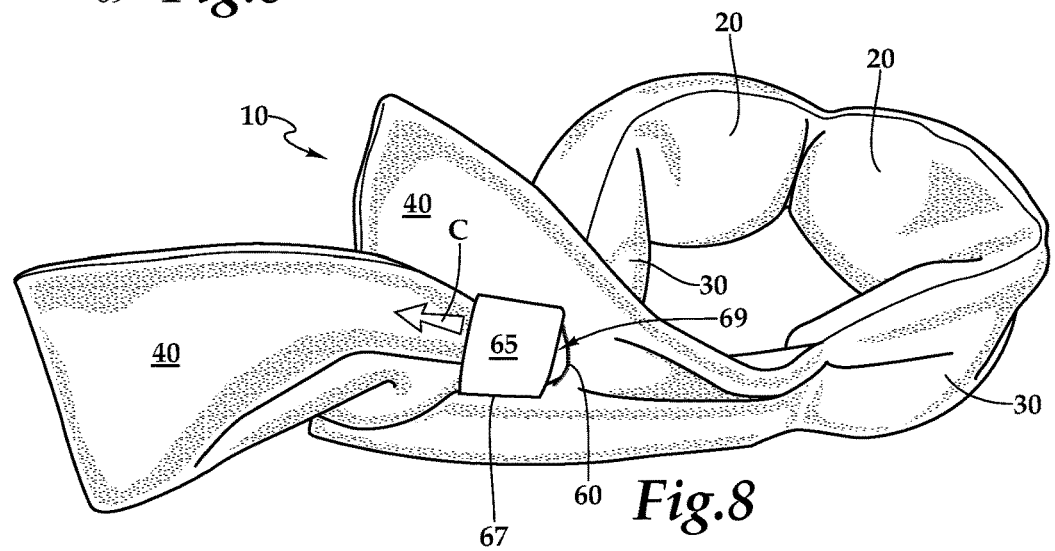
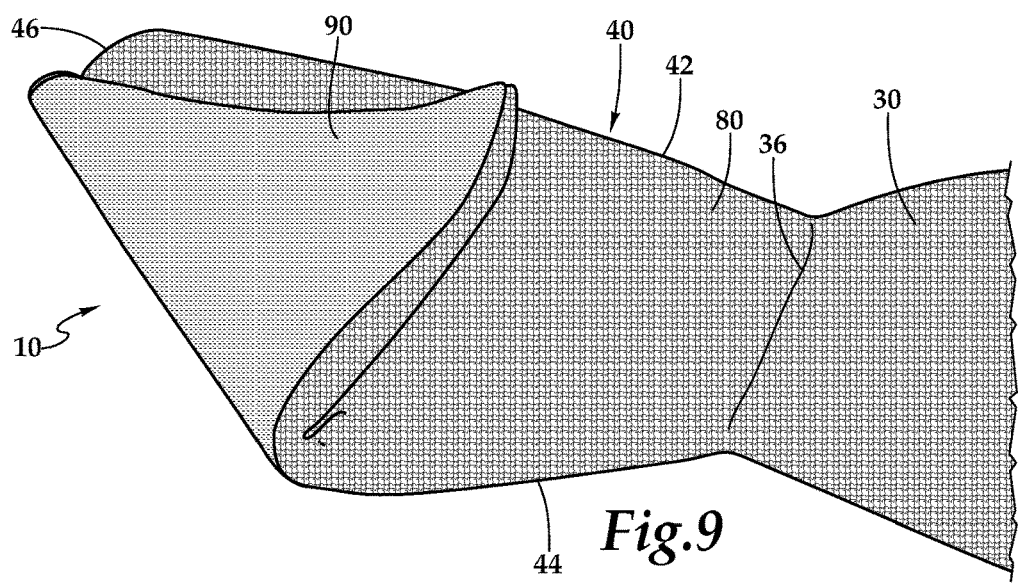

EYE COVERING PILLOW WITH HEAD ATTACHMENT

CROSS-REFERENCE TO RELATED APPLICATIONS

This application claims benefit under Title 35, United States Code § 119(e) of U.S. Provisional Application No. 62/396,976 filed on Sep. 20, 2016, and is a continuation-in-part of U.S. patent application Ser. No. 14/856,404, filed on Sep. 16, 2015 which is a continuation-in-part of U.S. patent application Ser. No. 12/799,413, filed on Apr. 22, 2010, issued on Sep. 22, 2015 as U.S. Pat. No. 9,138,086.

FIELD OF THE INVENTION

The following invention relates to eye coverings which wrap around a head of a person and cover eyes of the person, and optionally also ears of the user. More particularly, this invention relates to eye coverings in the form of a sleeve with media beads there in, divided into separate cells and with end structures which have retainer elements thereon which allow the end structures to be attached together and adjustably tightened to hold the eye covering upon the head of the user.

BACKGROUND OF THE INVENTION

Applicant's prior inventions relating to eye covering pillows are known to be provided either attached permanently or removably from a pillowcase or pillow, or to be provided separately without attachment to a pillow or pillowcase, but rather as an elongate multi-celled structure for wrapping about the head of a wearer when no pillow is involved. For instance, when riding in a car or on an airplane and desiring to have the benefits of light occlusion and tactile contact against the eyes, ears and other portions of the head of the wearer, the device without a pillow or pillowcase attached can be placed around a head of a wearer as a comfortable sleep aid.

Such placement with the prior eye covering can in some instances be difficult to maintain upon the head of the wearer. Different wearers have different head sizes, nose sizes, ear sizes, etc. and different amounts of hair which can cause the device to fall out of a desired position upon the head of the user. Furthermore, if the wearer is sitting upright versus laying down, gravity will tend to pull the device out of position over the eyes and other portions of the head of the wearer over time. Accordingly, a need exists for an eye covering which resists such displacement during use.

SUMMARY OF THE INVENTION

With this invention, a form of retainer is provided so that the eye covering of this invention can remain attached to a head of a wearer. In a first embodiment the eye covering is elongate in form and provided with four separate cells. Two central cells would typically be provided over eyes of the wearer, with two lateral cells closer to distal and proximal ends of the device might be placed over ears of the wearer. Further trapezoidal (or other shaped) end structures extend beyond these lateral cells somewhat and typically do not contain beads therein but merely are available for attachment as the device is wrapped around a head of a wearer. Thus, in one form, these ends can be tied together when the eye covering is wrapped about a head of a wearer. Such tying together or tucking beneath the head of a wearer can be effective when the wearer is lying down or when the head of the wearer and hair is sufficiently small that there is slack in the eye covering to allow for tying of these ends together.

Beneficially with this invention, and to further facilitate holding of these ends together, in this preferred embodiment a retainer, such as in the form of a slit, is provided in one of these end structures. While these distal or proximal end structures are shown as trapezoidal, they could have a variety of different geometric shapes. Preferably, one of these two end structures has a slit formed therein which is near a center point of the end structure. In the embodiment disclosed, an identifying tag is provided on one of these end structures. This slit is provided passing through the end structure directly adjacent to this tag. Thus, the tag can also be used to some extent to find this slit which might otherwise be difficult to locate.

The slit is just large enough to allow the opposite end structure to be fed through this slit. Material forming the end structures is sufficiently plush and padded and with a sufficient pile on a surface thereof that it has a relatively high degree of friction as it is passed into and out of this slit. Thus, it has a strong tendency to stay in position where it has been placed after having been fed partially through this slit. A greater or lesser amount of the end structure opposite the end structure having the slit therein can be fed through the slit so that a circumferential length remaining for the eye covering is adjusted to accommodate a circumferential size of a wearer's head. Thus, a properly fitting eye covering is always provided. Furthermore, the end section opposite the end section having the slit therein can be pulled a greater amount through the slit or a lesser amount through the slit to tighten the eye covering upon a head of a wearer. This tightening procedure can occur after the eye covering is already upon a head of a wearer by grasping and pulling the ends in opposite directions to provide final tightening and fine length and tightness adjustment.

As with previous embodiments, the two sides of the eye covering can have different fabric characteristics to provide a more warm or a more cool surface tactile function. With the slit as provided herein, the end structure opposite the end structure having the slit can be fed through the slit either to cause cool fabric to face inward towards eyes and other portions of the head of the wearer or for warm portions of the eye covering to extend inward towards eyes and other portions of the head of the wearer. Thus, with this slit such fastening facilitates reversibility to accommodate the needs and preferences of the user.

The size of the slit can be modified to increase or decrease the friction associated with passing the opposite end structure through this slit. Most preferably this slit has a length of about one inch with the width of the end structure being between about four inches and six inches. Other sizes of slits could alternatively be provided. While the slit is shown at a midpoint of one of the end structure, the slit could be located closer to a distal or proximal tip of the slitted end structure or closer to the cells which have beads or other media contained therein.

As an alternative to the retainer system utilizing the slit described above, a fastener could be provided, such as complemental hook and loop fastener structures located on the two ends, either on just one side of each end or on both sides of each end. Such complemental hook and loop fasteners could be such as those provided under the trademark VELCRO by Velcro Industries B.V. of the Netherlands.

As a further alternative fastener, complemental snaps could be provided on the ends to allow them to be snapped together, or buttons and slits could be provided for buttoning to fasten the ends together in a removable fashion. In the instance of utilization of hook and loop fasteners, or snaps or buttons and slits, either just a singular fastener half could be provided on each end or multiple such fastener halves could be provided at different locations on the ends to allow for adjustability of circumferential length between the fastener halves and to provide for fine adjustment of circumferential size of the eye covering.

While the slit of the preferred embodiment is shown passing entirely through one of the end structures, as an alternative, the tag could be sewn only at lateral edges and the tag could have an appropriate size so that the opposite end structure can be fed through a gap under the tag and the tag could act as a restraining loop to hold the opposite end structure to the end structure having the tag. Such a constraining loop could be provided separate from the tag as a further option. Thus, such a slit or a tag (or both) or other end structure retaining loop embody different forms of an end section retainer which allows a plain opposite end structure to be retained adjacent to an end structure which has been fitted with one of these retainers in the form of a slit, loop, tag or analogous structure. Thus, this invention includes either a fastener pair or a retainer system to provide an attachment structure to adjustably and removably hold ends of the eye covering together.

OBJECTS OF THE INVENTION

Accordingly, a primary object of the present invention is to provide an eye covering which can be easily and conveniently held around a head of a person and tightened around the head of a person for use both when sitting up and laying down.

Another object to the present invention is to provide an eye covering in the form of an elongate sleeve which can wrap around a head of a wearer and to be adjusted to limitless diameters for maximum comfort and secure holding to the head.

Another object of the present invention is to provide an eye covering in the form of an elongate sleeve which includes a retainer for holding end structures of the sleeve together, which retainer is of simple and reliable construction and which is easy to use.

Another object of the present invention is to provide a method for holding an eye covering structure to a head of a person and to adjust tightness of the eye covering.

Another object of the present invention is to enhance quality of sleep by providing an eye covering which includes cells filled with beads and with the cells formed of materials which provide a comfortable soft pressure against the eyes of the person and which can be adjusted to fit securely and comfortably to the user.

Other further objects of the present invention will become apparent from a careful reading of the included drawing figures, the claims and detailed description of the invention.

BRIEF DESCRIPTION OF THE DRAWINGS

FIG. 1 is a top plan view of the entire device of a preferred embodiment of this invention laying flat.

FIG. 2 is a front elevation view of that which is shown in FIG. 1.

FIG. 3 is left end view of that which is shown in FIG. 1

FIG. 4 is a perspective view of that which is shown in FIG. 1.

FIG. 5 is a perspective view of that which is shown in FIG. 1, positioned upon a head of a wearer, from the front and showing the four cells of beads in the sleeve resting over the two eyes and two ears of the wearer.

FIG. 6 is a perspective view similar to that which is shown in FIG. 5, but from the rear, and showing one end structure of the sleeve fed through the retainer slit in the other end structure.

FIG. 7 is a perspective view similar to that which is shown in FIG. 6, but with one end structure of the sleeve fed under the tag in the other end structure.

FIG. 8 is perspective view like FIG. 6, but with one end structure of the sleeve fed through both the slit and under the tag in the other end structure.

FIG. 9 is a detail of a portion of the sleeve end structure, with a corner folded over and showing that one surface is essentially smooth while the other surface has a fuzzy surface texture.

DESCRIPTION OF THE PREFERRED EMBODIMENT

Referring to the drawings, wherein like reference numerals represent like parts throughout the various drawing figures, reference numeral 10 is directed to an eye covering (FIGS. 1 and 4-8) in the form of an elongate sleeve of flexible fabric material broken into separate cells 20, 30 which are filled with media, such as plastic beads, with the cells 20, 30 positionable over eyes (and ears) on a head H of a user, while end structures 40 are held together by a retainer 50 to hold the eye covering 10 upon the head of the user.

In essence, and with particular reference to FIGS. 1-4, basic details of the eye covering 10 are described, according to a preferred embodiment. The eye covering 10 is an elongate sleeve of flexible fabric material. The sleeve is broken into cells 20, 30 including central cells 20 to be placed over eyes of a person, and lateral cells 30 to be placed over ears of a person. The sleeve ends at a first tip and a second tip defined as two opposite end structures 40. An attachment, such as a retainer 50 is associated with these end structures 40 to allow these two end structures 40 to be removably attached together to hold the eye covering 10 in a circular form to fit about a head of a person, and particularly to allow for tightening of the eye covering 10 so that it can hold securely to a head H of the user. This retainer 50 can include a slit 60 in one of the end structures 40 through which the other end structure 40 can pass, with a friction fit. A tag 65 defines one form of loop which can be provided adjacent to this slit, with a gap 69 under the tag 65 through which an opposite end structure 40 can pass. The tag 65 thus also acts as a form of retainer 50. The slit 60 and tag 65 can be used together in one embodiment. As another embodiment of the attachment, a hook and loop attachment 70 or other fastener (e.g. snaps) can be fitted to the end structures 40, to allow the end structures 40 to be removable attached to each other.

Applicant notes that a previous invention of applicant shared some similarity with this invention. The previous invention is described in U.S. Pat. No. 9,138,086, incorporated herein by reference in its entirety. Also, this application is directed to an invention which is a continuation-in-part of U.S. patent application Ser. No. 14/856,404, filed on Sep. 16, 2015, and also incorporated herein by reference in its entirety.

More specifically, and with particular reference to Figures at 1-5, basic details of the eye covering 10 are described, according to a preferred embodiment of this invention. The eye covering 10 is an elongate sleeve of flexible fabric material extending between a first tip and a second tip (also referred to as a proximal end and a distal end) defined in this preferred embodiment by opposite end structures 40, and with cells 20, 30 located therebetween. The sleeve forming the eye covering 10 has a hollow interior which is broken into separate cells by seams therebetween. These separate cells include central cells 20 and lateral cells 30.

The central cells 20 are bounded by top lateral facets 22 opposite bottom lateral facets 23 which preferably have a somewhat sinusoidal pattern which is similar for the top lateral facet 22 and for the bottom lateral facet 23, so that the form of the eye covering 10 alternates between shorter and taller and is reversible about a horizontal centerline. The shorter areas define seams including a central divider seam 26 and a pair of lateral divider seams 28 between the two central cells 20.

A nose arch 24 is defined in the bottom lateral facet 23 adjacent to the central divider seam 26 and provides a convenient location for a nose of a person wearing the eye covering 10 to be located, with the eye covering 10 just above the nose of the person. In this manner, the central cells 20 can be located with each of the central cells 20 located over one of the eyes of the person.

Each of the cells 20 is filled with media, such as in the form of plastic beads, rice, or other natural or synthetic media materials. This media gives a weight to the eye covering 10 and allows for the cells 20, 30 to be conformed in shape, and to provide a gentle pressure upon the person wearing the eye covering 10, which can be relaxing and promote quality sleep.

The fabric forming the sleeve of which the eye covering 10 is made, preferably it is two different types of fabric on front and rear surfaces of the eye covering 10. These different fabrics (FIG. 9) probably include one fabric which is smooth with little "fuzziness" and another side with a greater amount of "fuzziness." The greater fuzziness tends to allow air to be trapped adjacent thereto and provides for a lower rate of heat transfer from the eye covering 10 to the person wearing the eye covering 10. The smooth fabric side has less air trapped therein, and tends to promote heat transfer between the eye covering 10, thus allowing heat transfer from the media contained within eye covering 10, to the person wearing the eye covering 10.

These different rates of heat transfer cause the eye covering 10 to have a different apparent temperature to the person wearing the eye covering 10, depending on which surface of the eye covering 10 is placed against the face of the person. The human face is very sensitive to touch and temperature. A user can place the eye covering 10 against the face of the user, presenting the first side against the face of the user, and then presenting the second side against the face of the user, and the user can then make a determination as to which side is the most comfortable. For instance, if the user feels a little too hot, the user may select the side of the eye covering 10 which feels the coolest. If the user feels a little too cold, the user can select the side of the eye covering 10 which feels the warmest. Comfort is thus maximized.

Furthermore, the gentle pressure associated with the mass of the media and the ability of the media to conform to the face of the user, adjacent eyes of the user, provides gentle pressure which also promotes comfort and sleep. Utilizing the retainer 50 associate with the eye covering 10, the eye covering 10 can be held securely in place, not too loose and not too tight, so that the user can maximize the ability of the eye covering 10 to remain in position where desired on the head of the user and to best provide optimal gentle pressure and optimal apparent temperature, to promote peaceful sleep.

The lateral cells 30 are similar to the central cells 20, and located between the central cells 20 and each of the end structures 40. Each lateral cell includes top lateral facets 32 and bottom lateral facets 34 and extend past the lateral divider seems 28 where the lateral cells 30 join to the central cells 20, to end seams 36 where the lateral cells 30 transition into the end structures 40. Each of the seams 26, 28, 36 is preferably in the form of stitching passing through the sleeve of which the eye covering 10 is formed, to keep media contained within individual cells between the seams 26, 28, 36, rather than being able to freely float therebetween.

Each of the cells 20, 30 preferably has a similar number of media pieces within each cell 20, 30. The lateral cells 30 are positioned to fit over ears of the user. These lateral cells 30 tend to deaden sound and provide comfort touch to ears of the user. As with the central cells 20, the lateral cells 30 preferably have a sinusoidal top and bottom edge form which causes the lateral cells 30 to transition between shorter and taller with taller portions of the lateral cells 30 adjacent portions of each lateral cell 30, and shortest portions of each lateral cell 30 adjacent to the end seams 36 and lateral divider seams 28 on either lateral edge of the lateral cells 30.

The end structures 40 are preferably similar in form and preferably trapezoidal. The end structures 40 thus have two parallel sides which are opposite each other and two non-parallel sides which are opposite each other. The two parallel sides preferably include the end edge 46 and the end seams 36 with the end structure 40 therebetween. The top edge 42 about a bottom edge 44 preferably diverge away from each other as they extend from the end seams 36 toward the end edge 46.

Because the end edge 46 is longer than the end seams 36, once an end structure 40 has been pushed through either the slit 60 of the retainer 50 or the gap 69 under the tag 65 (or other loop) of the retainer 50 (or through both the slit 60 and gap 69) the end structure 40 will tend to hold its position therein. Because the end structure 40 is formed of flexible fabric material, it can readily be pushed through the slit 60 and/or under the tag 65. Preferably the end structures 40 are not filled with media or only a small amount of media, to further facilitate passage of the end structures 40 at one end of the eye covering 20 through the slit 60 or under the tag 65 of the other end structure 40. A center point 48 of one of the end structures 40 provides a location which is preferred for the slit 60 and with the tag 65 directly adjacent to the slit 60, typically closer to the end edge 46, but alternatively with the tag 65 adjacent to the slit 60 and having some other orientation relative to the end edge 46.

The slit 60 provides a preferred form of retainer 50 for holding the end structures 40 together. This slit 60 is similar to a button hole which includes opposite corners 62 and opposite sides 64. The slit 60 preferably does not have any fabric therebetween, but rather is merely a cut in the fabric forming the end structure 40 bearing the slit 60, and located near a center point 48 of this end structure 40. A perimeter of the slit 60 is typically hemmed (or otherwise finished) to prevent fraying of the fabric, and to join front and back portions of the sleeve together so that the slit 60 passes from the front side of the eye covering 10 to the back side of the eye covering 10, rather than passing through and into an interior of the sleeve forming the eye covering 10.

The slit 60 is preferably of a length of about one inch between the corners 62 in embodiments where the end edge 46 of the end structure 40 is approximately six inches and with the overall length of the eye covering being approximately thirty-two inches. The cells are preferably about 3½ inches tall and about 3½ inches wide. Other dimensions could be utilized, such as to accommodate different size users.

As an additional or alternative form of retainer 50, the tag 65 is sewn to one of the end structures 40, and is provided with a gap 69 underneath the tag 65 extending between edges 67 where the tag 65 is sewn to adjacent end structures 40. The tag 65 thus creates a form of a loop through which an opposite end structure 40 can pass, through the gap 69 beneath the tag 65. The tag 65 is itself preferably flexible fabric which typically bears information about the eye covering 10 product to communicate such information to a user. This flexible fabric tag 65 has each of its edges 67 sewn to one of the end structures 40 with the gap 69 therebetween. Preferably this gap 69 between the two edges 67 is about 1½ inches long. A user can take an end structure 40 opposite the end structure 40 bearing the slit 60 and/or tag 65, and feed that opposite end structure 40 through either the slit 60 or under the tag 65 (or both) and then feeding the opposite end structure 40 through the slit 60 and/or gap 69 and pull on this opposite end structure 40 until it is tight about a head H of a user. This simple and efficient attachment and tightening method allows the user to easily and appropriately tighten the eye covering 10 about the head H of the user. FIGS. 6-8 show these various tightening methodologies.

As an alternative, the end structures 40 of the eye covering 10 could include other attachments, such as various different portions of a hook and loop attachment 70, such as a hook patch 72 attached to one of the end structures 40 and a loop patch 74 attached to the other end structure 40 (or other fasteners, such as snaps). The end structures 40 can thus be brought together and then removably attached together through this hook and loop attachment 70. The hook patch 72 a loop patch 74 can be provided on a common front or rear surface of the eye covering 10, or on opposite front/rear or rear/front surfaces of the eye covering 10. If on opposite surfaces, an overlapping attachment joint is provided. If both are on the same surface, then the sides bearing the patches 72, 74 would be brought together in a non-overlapping joint fashion. Preferably hook and loop attachment 70 materials are configured to be of a type which does not tend to grasp human hair, such that the inconvenience of having the hook and loop fastener pull at hair of the user can be avoided.

This disclosure is provided to reveal a preferred embodiment of the invention and a best mode for practicing the invention. Having thus described the invention in this way, it should be apparent that various different modifications can be made to the preferred embodiment without departing from the scope and spirit of this disclosure. When structures are identified as a means to perform a function, the identification is intended to include all structures which can perform the function specified.

What is claimed is:

1. An eye covering, comprising in combination:
    a plurality of fabric cells provided in an elongate chain between a distal end and a proximal end;
    said fabric cells each having two surfaces including a front surface opposite a rear surface, said surfaces formed of different types of fabrics;
    media contained within said cells;
    a first end structure adjacent to one of said cells at said distal end;
    a second end structure adjacent one of said cells at said proximal end;
    at least one of said first and second end structures having an attachment thereon attaching to the other one of said first and second end structures to hold said eye covering in a ring for wearing over eyes and about a head of a user;
    wherein said attachment structure includes a retainer on one of said first and second end structures to hold the other of said first and second end structures;
    wherein said retainer includes a slit passing through one of said first and second end structures; and
    wherein said retainer also includes a loop coupled to one of said end structures, said loop large enough to allow the other of said end structures to pass at least partially therethrough.

2. The eye covering of claim 1 wherein said two surfaces exhibit different rates of heat transfer.

3. An eye covering with head attachment, comprising in combination:
    an elongate sleeve extending from a first tip to a second tip, with media contained within at least portions of said sleeve;
    said sleeve divided into a plurality of fabric cells, each of said fabric cells having two surfaces including a front surface opposite a rear surface, said two surfaces formed of different types of fabric;
    a first end structure adjacent to said first tip;
    a second end structure adjacent to said second tip;
    said first end structure having a retainer thereon, said retainer holding said second end structure to said first end structure;
    wherein said retainer includes a slit passing through said first end structure;
    wherein said second end structure has a shape which is wider adjacent said second tip than portions of said second end structure closer to a center of said sleeve between said first tip and said second tip when said elongate sleeve is laying flat;
    wherein said second end structure is trapezoidal in form with a pair of parallel sides having different lengths, and with a longer one of said parallel pair of sides located most distant from said first end structure when said elongate sleeve is laying flat; and
    wherein said first end structure includes a loop adjacent to said slit, said loop having opposite edges attached to said first end structure and with a gap between said opposite edges wherein said loop is not attached to and placeable away from said first end structure, said second end structure fed through said slit and through said gap beneath said loop.

4. The eye covering of claim 3 wherein said elongate sleeve includes two central cells spaced apart by a central divider seam, said two central cells extending up to top lateral facets and extending down to bottom lateral facets, a nose arch located within said bottom lateral facet, said nose arch adjacent to said central divider seam, said top lateral facets and said bottom lateral facet being mirror images of each other about a horizontal centerline, such that said eye covering is reversible about said horizontal center line, and with media beads located within each of said two central cells.

5. The eye covering of claim 4 wherein each of said end structures is free of media therein and exhibit a trapezoidal shape with two parallel sides of different lengths, and with a longest parallel side of each said end structure located at said first tip and said second tip.

6. The eye covering of claim 5 wherein said retainer includes a slit passing through said first end structure, and wherein said second end structure has a shape which is wider adjacent said second tip than portions of said second end structure closer to a center of said sleeve between said first tip and said second tip, when said elongate sleeve is laying flat.

7. The eye covering of claim 3 wherein said two surfaces exhibit different rates of heat transfer.

8. A method for holding an eye covering upon a head of a person and over eyes of the person, the method including the steps of:

placing an eye covering over eyes of a person, the eye covering having an elongate sleeve extending from a first tip to a second tip, with media contained within at least portions of said sleeve, a first end structure adjacent to the first tip, a second end structure adjacent to the second tip, the first end structure having a retainer thereon;

attaching the second end structure to the first end structure through the retainer;

wherein said attaching step includes the first end structure having a loop, the loop having opposite edges attached to the first end structure and with a gap between the opposite edges where the loop is not attached to and placeable away from the first end structure;

feeding the second end structure through the gap beneath the loop;

wherein said attaching step further includes a slit located in said first end structure adjacent to the loop;

wherein said feeding step includes feeding the second end structure through both the slit and through the gap beneath the loop; and tightening the sleeve by pulling on a portion of the second end structure beyond the slit and the loop to pull the second end structure through the slit and through the gap beneath the loop, until the elongate sleeve is tight about the head of the person.

\* \* \* \* \*